United States Patent
Nagata et al.

(10) Patent No.: US 10,716,540 B2
(45) Date of Patent: Jul. 21, 2020

(54) RESIN COMPOSITION FOR ACOUSTIC WAVE PROBE, AND ACOUSTIC LENS USING THE SAME, ACOUSTIC WAVE PROBE, ACOUSTIC WAVE MEASUREMENT APPARATUS, ULTRASOUND DIAGNOSTIC APPARATUS, PHOTOACOUSTIC WAVE MEASUREMENT APPARATUS, AND ULTRASOUND ENDOSCOPE

(71) Applicant: FUJIFILM Corporation, Tokyo (JP)

(72) Inventors: Yuzo Nagata, Kanagawa (JP); Yoshihiro Nakai, Kanagawa (JP); Shigeki Uehira, Kanagawa (JP); Atsushi Osawa, Kanagawa (JP)

(73) Assignee: FUJIFILM Corporation, Tokyo (JP)

(*) Notice: Subject to any disclaimer, the term of this patent is extended or adjusted under 35 U.S.C. 154(b) by 5 days.

(21) Appl. No.: 16/143,712

(22) Filed: Sep. 27, 2018

(65) Prior Publication Data
US 2019/0023831 A1 Jan. 24, 2019

Related U.S. Application Data
(63) Continuation of application No. PCT/JP2017/011980, filed on Mar. 24, 2017.

(30) Foreign Application Priority Data
Mar. 29, 2016 (JP) .................. 2016-066427

(51) Int. Cl.
| | |
|---|---|
| A61B 8/00 | (2006.01) |
| C08G 18/61 | (2006.01) |
| C08G 18/76 | (2006.01) |
| C08G 18/48 | (2006.01) |
| C08G 18/73 | (2006.01) |
| C08G 77/452 | (2006.01) |
| A61B 5/00 | (2006.01) |
| A61B 8/12 | (2006.01) |
| G10K 11/30 | (2006.01) |

(52) U.S. Cl.
CPC ........ *A61B 8/4444* (2013.01); *C08G 18/4833* (2013.01); *C08G 18/61* (2013.01); *C08G 18/73* (2013.01); *C08G 18/7671* (2013.01); *C08G 18/7678* (2013.01); *C08G 77/452* (2013.01); *A61B 5/0095* (2013.01); *A61B 8/12* (2013.01); *G10K 11/30* (2013.01)

(58) Field of Classification Search
CPC ............................ C08G 77/452; C08G 77/80
See application file for complete search history.

(56) References Cited

U.S. PATENT DOCUMENTS
| | | |
|---|---|---|
| 4,651,850 A | 3/1987 | Matsuo |
| 2005/0070801 A1 | 3/2005 | Yamashita et al. |
| 2006/0014916 A1* | 1/2006 | Yilgor ............. C08G 18/10 528/25 |
| 2009/0069486 A1 | 3/2009 | Yamashita et al. |
| 2012/0232217 A1* | 9/2012 | Pfeiffer ........... C08G 18/2825 524/588 |
| 2016/0264709 A1* | 9/2016 | Smith ............. C08G 18/5024 |

FOREIGN PATENT DOCUMENTS
| | | | |
|---|---|---|---|
| CN | 105273594 | * | 1/2016 |
| JP | 58-216294 A | | 12/1983 |
| JP | 08-000615 A | | 1/1996 |
| JP | 2002-095081 A | | 3/2002 |
| JP | 2005-125071 A | | 5/2005 |
| JP | 2011-212084 A | | 10/2011 |
| JP | 2014-188009 A | | 10/2014 |

OTHER PUBLICATIONS
"Segmented Organosiloxane Copolymers. 1. Synthesis of Siloxane-urea Copolymers" authored by Yilgor et al. and published in Polymer (1984) 25, 1800-1806.*
International Search Report dated Jun. 13, 2017 by the International Searching Authority in International Patent Application No. PCT/JP2017/011980.
Written Opinion dated Jun. 13, 2017 by the International Searching Authority in International Patent Application No. PCT/JP2017/011980.
International Preliminary Report on Patentability with translation of Written Opinion dated Oct. 2, 2018, from the International Bureau in counterpart International Application No. PCT/JP2017/011980.

* cited by examiner

*Primary Examiner* — Marc S Zimmer
(74) *Attorney, Agent, or Firm* — Sughrue Mion, PLLC

(57) ABSTRACT

Provided are a resin composition for an acoustic wave probe including, a polymer which has a structural unit having a siloxane bond and a structural unit having a urea bond, an acoustic lens using the same, the acoustic wave probe, acoustic wave measurement apparatus, ultrasound diagnostic apparatus, photoacoustic wave measurement apparatus, and ultrasound endoscope.

12 Claims, 1 Drawing Sheet

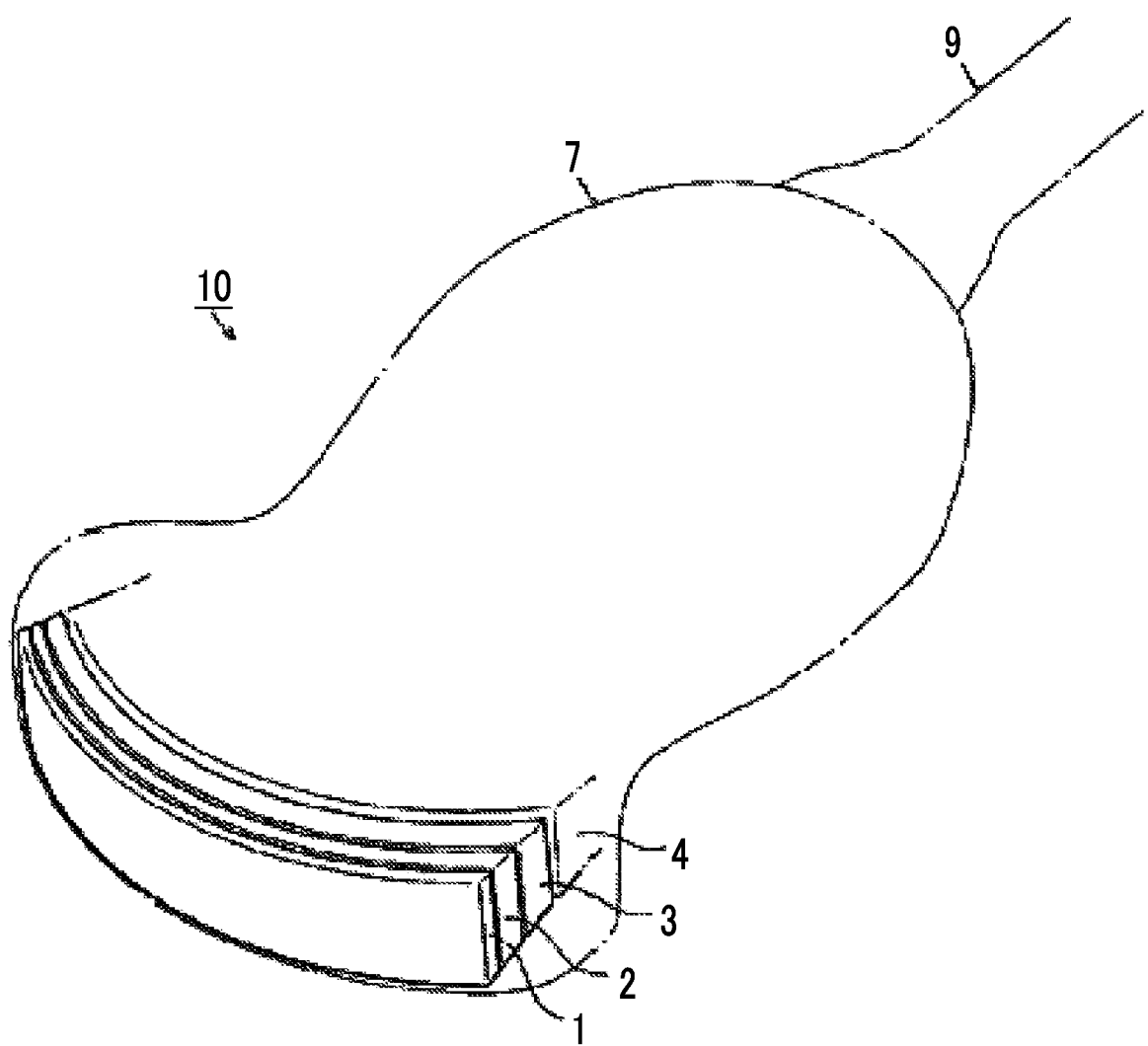

RESIN COMPOSITION FOR ACOUSTIC WAVE PROBE, AND ACOUSTIC LENS USING THE SAME, ACOUSTIC WAVE PROBE, ACOUSTIC WAVE MEASUREMENT APPARATUS, ULTRASOUND DIAGNOSTIC APPARATUS, PHOTOACOUSTIC WAVE MEASUREMENT APPARATUS, AND ULTRASOUND ENDOSCOPE

CROSS-REFERENCE TO RELATED APPLICATIONS

This application is a Continuation of PCT International Application No. PCT/JP2017/011980 filed on Mar. 24, 2017, which claims priority under 35 U.S.C. § 119 (a) to Japanese Patent Application No. 2016-066427 filed in Japan on Mar. 29, 2016. Each of the above applications is hereby expressly incorporated by reference, in its entirety, into the present application.

BACKGROUND OF THE INVENTION

1. Field of the Invention

The present invention relates to a resin composition for an acoustic wave probe, an acoustic lens using the same, and the acoustic wave probe. Furthermore, the present invention relates to an acoustic wave measurement apparatus, an ultrasound diagnostic apparatus, a photoacoustic wave measurement apparatus, and an ultrasound endoscope.

2. Description of the Related Art

In the acoustic wave measurement apparatus, an acoustic wave probe is used which irradiates a test object or a site (hereinafter, simply referred to as an object) with an acoustic wave, receives a reflected wave (echo) thereof, and outputs a signal. An electrical signal converted from the reflected wave which has been received by this acoustic wave probe is displayed as an image. Accordingly, the interior of the test object is visualized and observed.

Acoustic waves, such as ultrasonic waves and photoacoustic waves, which have an appropriate frequency in accordance with a test object and/or measurement conditions, are selected as the acoustic waves.

For example, the ultrasound diagnostic apparatus transmits an ultrasonic wave to the interior of a test object, receives the ultrasonic wave reflected by the tissues inside the test object, and displays the received ultrasonic wave as an image. The photoacoustic wave measurement apparatus receives an acoustic wave radiated from the interior of a test object due to a photoacoustic effect, and displays the received acoustic wave as an image. The photoacoustic effect is a phenomenon in which an acoustic wave (typically an ultrasonic wave) is generated through thermal expansion after a test object absorbs an electromagnetic wave and generates heat in a case where the test object is irradiated with an electromagnetic wave pulse of visible light, near infrared light, microwave, or the like.

The acoustic wave measurement apparatus performs transmission and reception of an acoustic wave on a living body (typically, the human body) which is a test object. Therefore, it is necessary to fulfill requirements such as consistency in the acoustic impedance within the living body and decrease in acoustic attenuation.

For example, a probe for an ultrasound diagnostic apparatus (also referred to as an ultrasound probe) which is a kind of acoustic wave probe includes a piezoelectric element which transmits and receives an ultrasonic wave and an acoustic lens which is a portion coming into contact with a living body. An ultrasonic wave generated from the piezoelectric element is incident on the living body after being transmitted through the acoustic lens. In a case where the difference between acoustic impedance (density×acoustic velocity) of the acoustic lens and acoustic impedance of the living body is large, the ultrasonic wave is reflected by the surface of the living body. Therefore, the ultrasonic wave is not efficiently incident on the living body. For this reason, it is difficult to obtain a favorable resolution. In addition, it is desirable that ultrasonic attenuation of the acoustic lens is low in order to transmit and receive the ultrasonic wave with high sensitivity.

For this reason, silicone resin of which the acoustic impedance is close to the acoustic impedance (in the case of a human body, $1.4 \times 10^6$ to $1.7 \times 10^6$ $kg/m^2/sec$) of a living body and which has a low ultrasonic attenuation is used as a material of the acoustic lens. For example, JP1996-615A (JP-H08-615A) discloses an acoustic lens of a contactor for an ultrasound diagnostic apparatus formed of a mixture of silicone rubber and butadiene rubber.

In addition, JP2002-095081A discloses an ultrasound terminal obtained by vulcanizing and molding a composition in which silicone rubber is filled with silica particles, with a vulcanizing agent. JP1983-216294A (JP-S58-216294A) discloses an acoustic lens obtained by mixing titanium oxide with silicone rubber and JP2005-125071A discloses an acoustic lens composition containing silicone rubber and zinc oxide powder.

SUMMARY OF THE INVENTION

Resin made of silicone is soft and has a low mechanical strength. For this reason, inorganic filler (also referred to as inorganic filling agent) is formulated for the purpose of improving hardness and the mechanical strength (such as JP2002-095081A, JP1983-216294A (JP-S58-216294A), and JP2005-125071A). However, in a case of intending to achieve the required mechanical strength, the amount of inorganic filler added to the silicone resin inevitably increases. For this reason, ultrasonic waves are scattered and acoustic attenuation increases. In particular, there is a problem in that the acoustic attenuation increases as the frequency increases.

In view of the above-described circumstances, an object of the present invention is to provide a resin composition for an acoustic wave probe with which it is possible to obtain a resin sheet in which the acoustic impedance is close to an acoustic impedance value of a living body by molding the resin composition for an acoustic wave probe into a sheet shape, and the acoustic attenuation decreases even at a high frequency (for example, 10 MHz), and which has an excellent tear strength.

In addition, another object of the present invention is to provide an acoustic lens using the above-described resin composition for an acoustic wave probe, the acoustic wave probe, an acoustic wave measurement apparatus, an ultrasound diagnostic apparatus, a photoacoustic wave measurement apparatus, and an ultrasound endoscope.

The present inventors have conducted extensive studies. As a result, they have found that a resin composition for an acoustic wave probe containing a specific polymer which has a structural unit having a siloxane bond and a structural unit having a urea bond can solve the above-described objects, and have completed the present invention based on the findings.

The above-described objects are solved by the following means.

(1) A resin composition for an acoustic wave probe comprising: a polymer which has a structural unit having a siloxane bond and a structural unit having a urea bond.

(2) The resin composition for an acoustic wave probe according to (1), in which the structural unit having a siloxane bond is represented by General Formula (1) and the structural unit having a urea bond is represented by General Formula (2).

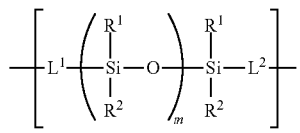

General Formula (1)

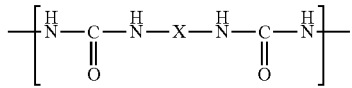

General Formula (2)

In the formulae, $R^1$ and $R^2$ each independently represent a monovalent organic group, $L^1$ and $L^2$ each independently represent a single bond or a divalent linking group, X represents a divalent linking group. m represents an integer of 1 to 10,000.

(3) The resin composition for an acoustic wave probe according to (1) or (2), in which an amount of urea in the polymer is 0.2 to 3.0 mmol/g.

(4) The resin composition for an acoustic wave probe according to any one of (1) to (3), in which a mass average molecular weight of the polymer is greater than or equal to 100,000.

(5) The resin composition for an acoustic wave probe according to any one of (1) to (4), in which a proportion of the structural unit having a siloxane bond in the polymer is greater than or equal to 70 mass %.

(6) The resin composition for an acoustic wave probe according to any one of (1) to (5), in which a density of the polymer is greater than or equal to 1.1 g/cm$^3$.

(7) The resin composition for an acoustic wave probe according to any one of (1) to (6), in which the structural unit having a urea bond has an aromatic ring.

(8) The resin composition for an acoustic wave probe according to any one of (1) to (7), in which the structural unit having a siloxane bond has an aromatic ring.

(9) An acoustic lens comprising: the resin composition for an acoustic wave probe according to any one of (1) to (8).

(10) An acoustic wave probe comprising: the acoustic lens according to (9).

(11) An acoustic wave measurement apparatus comprising: the acoustic wave probe according to (10).

(12) An ultrasound diagnostic apparatus comprising: the acoustic wave probe according to (10).

(13) A photoacoustic wave measurement apparatus comprising: the acoustic lens according to (9).

(14) An ultrasound endoscope comprising: the acoustic lens according to (9).

Unless otherwise specified in the description of the present specification, in a case where there are groups having a plurality of the same reference numerals as each other in general formulae representing compounds, these may be the same as or different from each other, and a group (for example, an alkyl group) specified by each group may further have a substituent. In addition, the "Si—H group" means a group having three bonds on a silicon atom, but the description of the bonds is not repeated and the notation is simplified.

In addition, in the present specification, "to" means a range including numerical values denoted before and after "to" as a lower limit value and an upper limit value.

Unless otherwise specified, the mass average molecular weight in the present specification refers to a value (in terms of polystyrene) measured through gel permeation chromatography (GPC).

By molding (preferably press-molding) the resin composition for an acoustic wave probe of the present invention into a sheet shape, it is possible to provide a resin sheet for an acoustic wave probe in which the acoustic impedance is close to an acoustic impedance value of a living body, and the acoustic attenuation decreases even at a high frequency, and which has an excellent tear strength. In addition, it is possible to provide an acoustic lens using the resin sheet formed of the above-described resin composition for an acoustic wave probe having the excellent performances, the acoustic wave probe, an acoustic wave measurement apparatus, an ultrasound diagnostic apparatus, a photoacoustic wave measurement apparatus, and an ultrasound endoscope.

The above-described characteristics and advantages and other characteristics and advantages of the present invention become clearer in the following descriptions with reference to the accompanying drawing.

BRIEF DESCRIPTION OF THE DRAWING

FIG. 1 is a perspective transparent view of an example of a convex ultrasound probe which is an embodiment of an acoustic wave probe.

DESCRIPTION OF THE PREFERRED EMBODIMENTS

<<Resin Composition for Acoustic Wave Probe>>

The resin composition for an acoustic wave probe of the present invention (hereinafter, also simply referred to as a resin composition) contains a polymer (hereinafter, also referred to as a specific polymer) which has a structural unit (a) having a siloxane bond and a structural unit (b) having a urea bond.

The resin composition for an acoustic wave probe of the present invention may be formed of a specific polymer or may contain commonly used components such as other additives described below or optional components expressing an additional action, in addition to the specific polymer. In a case where the resin composition for an acoustic wave probe of the present invention is formed of two or more components, in general, it is preferable that the resin composition for an acoustic wave probe is in a form of a composition in which the components are homogeneously mixed with each other.

The shape of the resin composition for an acoustic wave probe itself of the present invention is not particularly limited. The resin composition for an acoustic wave probe may be mixed with a solvent or the like and have fluidity, or may have a pellet shape.

By molding (preferably pressurizing) the resin composition for an acoustic wave probe of the present invention into a sheet shape, it is possible to provide a resin sheet having all excellent characteristics of an acoustic impedance close to an acoustic impedance value of a living body, decrease in an acoustic attenuation (particularly an acoustic attenuation at a high frequency), and an excellent tear strength. Although the action and the mechanism thereof are unclear and estimated, those are thought as follows.

Although the acoustic attenuation favorably decreases in silicone resin alone in the related art, the film hardness is low. It is considered that the low film hardness is caused by a small interaction between silicone resins. On the other hand, since the specific polymer used in the present invention has a hydrogen-bondable urea bond, it is considered that the interaction between specific polymers increases and the film hardness of an obtained resin sheet is improved. That is, it is possible to achieve both the decrease in acoustic attenuation and the high film hardness. In addition, since the specific polymer used in the present invention has the above-described structural units (a) and (b), the density of the specific polymer is high. For this reason, it is considered that the acoustic impedance of a resin sheet obtained by processing the resin composition for an acoustic wave probe of the present invention can be set to an acoustic impedance value close to a living body.

Accordingly, even in a case where the resin composition for an acoustic wave probe of the present invention does not contain inorganic filler, it is possible to produce a resin sheet exhibiting the above-described excellent characteristics.

Hereinafter, a resin sheet obtained from the resin composition for an acoustic wave probe of the present invention is also referred to as a "resin sheet for an acoustic wave probe" or a "resin sheet".

1) Polymer which has Structural Unit (a) having Siloxane Bond and Structural Unit (b) having Urea Bond.

The structure of the specific polymer used in the present invention is not particularly limited and examples thereof include a random structure, a block structure, and a graft structure. However, a block structure is preferable from the viewpoint of imparting film hardness to an acoustic lens or the like produced using the resin composition of the present invention.

In addition, the urea bond in the structural unit (b) having a urea bond may be introduced into either a main chain and/or a side chain in the specific polymer, but it is preferably introduced into a main chain.

As the specific polymer used in the present invention, a polymer in which the structural unit (a) having a siloxane bond is represented by General Formula (1) and the structural unit (b) having a urea bond is represented by General Formula (2) is preferable from the viewpoint of imparting film hardness.

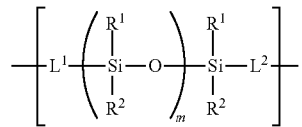
General Formula (1)

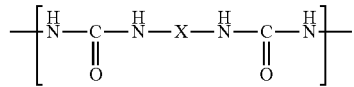
General Formula (2)

In the formulae, $R^1$ and $R^2$ each independently represent a monovalent organic group, $L^1$ and $L^2$ each independently represent a single bond or a divalent linking group, X represents a divalent linking group. m represents an integer of 1 to 10,000.

As the monovalent organic groups of $R^1$ and $R^2$, any one of an alkyl group, a cycloalkyl group, an alkenyl group, and an aryl group is preferable. Hereinafter, the details will be described below.

The number of carbon atoms in an alkyl group is preferably 1 to 10, more preferably 1 to 4, still more preferably 1 or 2, and particularly preferably 1. Examples of the alkyl group include a methyl group, an ethyl group, an n-propyl group, an isopropyl group, an n-butyl group, an isobutyl group, an n-hexyl group, an n-octyl group, a 2-ethylhexyl group, and an n-decyl group.

The number of carbon atoms in a cycloalkyl group is preferably 3 to 10, more preferably 5 to 10, and still more preferably 5 or 6. In addition, the cycloalkyl group is preferably a 3-membered ring, a 5-membered ring, or a 6-membered ring, and more preferably a 5-membered ring or a 6-membered ring. Examples of the cycloalkyl group include a cyclopropyl group, a cyclopentyl group, and a cyclohexyl group.

The number of carbon atoms in an alkenyl group is preferably 2 to 10, more preferably 2 to 4, and still more preferably 2. Examples of the alkenyl group include a vinyl group, an allyl group, and a butenyl group.

The number of carbon atoms in an aryl group is preferably 6 to 12, more preferably 6 to 10, and still more preferably 6 to 8. Examples of the aryl group include a phenyl group, a tolyl group, and a naphthyl group.

The alkyl group, the cycloalkyl group, the alkenyl group, and the aryl group may have a substituent. Examples of such a substituent include a halogen atom, an alkyl group, a cycloalkyl group, an alkenyl group, an aryl group, an alkoxy group, an aryloxy group, an alkylthio group, an arylthio group, a silyl group, and a cyano group.

Examples of the group having a substituent include a halogenated alkyl group.

$R^1$ and $R^2$ are preferably an alkyl group, an alkenyl group, or an aryl group, more preferably an alkyl group having 1 to 4 carbon atoms, a vinyl group, or a phenyl group, still more preferably a methyl group, a vinyl group, or a phenyl group, and particularly preferably a methyl group or a phenyl group.

It is most preferable that $R^1$ and $R^2$ are both phenyl groups from the viewpoint of acoustic impedance.

The divalent linking groups of $L^1$ and $L^2$ are not particularly limited as long as the effect of the present invention is exhibited, and examples thereof include alkylene groups (the number of carbon atoms is preferably 1 to 12, more preferably 1 to 8, still more preferably 1 to 6, and particularly preferably 1 to 3, and specific examples thereof include methylene, ethylene, n-propylene, isopropylene, n-butylene, t-butylene, and n-octylene), arylene groups (the number of carbon atoms is preferably 6 to 18, more preferably 6 to 14, and still more preferably 6 to 12, and specific examples thereof include phenylene, tolylene, and naphthylene), oxyalkylene groups (the number of carbon atoms is preferably 1 to 12, more preferably 1 to 8, still more preferably 1 to 6, and particularly preferably 1 to 3, and specific examples thereof include oxymethylene, oxyethylene, oxypropylene, and oxy dimethyl ethylene), and oxyaryl groups (the number of carbon atoms is preferably 6 to 18, more preferably 6 to 14, and particularly preferably 6 to 12, and specific examples thereof include oxyphenylene, oxytolylene, and oxynaphthylene), and alkylene groups or oxyalkylene groups are preferable.

The oxyalkylene group and the oxyarylene group described above may be bonded to adjacent to Si on either side of an oxy group and an alkylene group or an arylene group, but are preferably bonded to adjacent Si on an alkylene group and an arylene group and more preferably a methylene group or a phenylene group.

The divalent linking group of X is not particularly limited as long as the effect of the present invention is exhibited, but examples thereof include a divalent linking group selected from an alkylene group, an arylene group, —O—, —S—, —C(=O)O— and —NR$^N$C(=O)— (R$^N$ represents a hydrogen atom, an alkyl group, or an aryl group), and a group obtained by combining the divalent linking groups. The description of the alkylene group and the arylene group in L$^1$ and L$^2$ can be preferably applied to the alkylene group and the arylene group.

An alkylene group or an arylene group is preferable as a group formed of the above-described divalent linking group alone.

Preferred examples of the group obtained by combining the above-described divalent linking groups (the number of combinations is not particularly limited) include an alkylene-arylene group, an alkylene-arylene-alkylene group, and an arylene-alkylene-arylene group, and a specifically preferred example thereof includes diphenylmethane-4,4'-diyl.

The divalent linking group of X is preferably any one of an alkylene group, an arylene group, and an arylene-alkylene-arylene group. From the viewpoint of the acoustic impedance, X preferably has an aromatic ring which will be described below and is more preferably any one of an arylene group and an arylene-alkylene-arylene group.

m is preferably an integer of 1 to 1,000 and more preferably an integer of 10 to 100.

The amount of urea in the specific polymer is preferably 0.2 to 3.0 mmol/g, more preferably 0.4 to 1.5 mmol/g, still more preferably 0.5 to 1.5 mmol/g, and particularly preferably 0.5 to 1.0 mmol/g. In a case where the amount of hydrogen-bondable urea bond in the polymer is within the above-described ranges, it is possible to reduce the acoustic attenuation of the resin composition of the present invention while imparting high film hardness.

Here, the amount of urea in the specific polymer can be calculated, for example, from the amount of isocyanate monomer charged during synthesis based on the following equation. However, the isocyanate monomer means a compound having an isocyanate group capable of forming a urea bond in a polymer. In the following equation, it is assumed that only a urea bond is formed by a reaction of isocyanate groups in all the isocyanate monomers charged during synthesis.

Amount of urea (mmol/g)=number of isocyanate groups in one molecule of isocyanate monomer×amount of isocyanate monomer (mmol)/total amount of specific polymer (g)

From the viewpoint of imparting film hardness, it is preferable that the molecular weight of the specific polymer is high. The mass average molecular weight is preferably greater than or equal to 100,000, more preferably 100,000 to 3,000,000, and still more preferably 200,000 to 1,000,000.

In the specific polymer, the proportion of the structural unit (a) having a siloxane bond is preferably greater than or equal to 70 mass %, more preferably 70 to 98 mass %, and still more preferably 70 to 92 mass %, from the viewpoint of making the acoustic impedance be close to an acoustic impedance value of a living body and reducing the acoustic attenuation.

In addition, the proportion of the structural unit (b) having a urea bond in the specific polymer is preferably 3 to 30 mass % and more preferably 5 to 30 mass %, from the viewpoint of imparting high film hardness and making the acoustic impedance be close to an acoustic impedance value of a living body.

Here, the content of the structural unit (a) having a siloxane bond and the structural unit (b) having a urea bond in the specific polymer can be calculated, for example, from the charged amount (mass ratio) of a monomer having a siloxane bond and a monomer having an isocyanate group during synthesis.

The acoustic impedance of the resin sheet obtained from the resin composition of the present invention is preferably close to an acoustic impedance value of a living body, more preferably 1.3 Mrayls, that is, greater than or equal to 1.3×10$^6$ kg/m$^2$/s. Therefore, the density of the specific polymer is preferably greater than or equal to 1.0 g/cm$^3$ and more preferably greater than or equal to 1.1 g/cm$^3$. Here, the value of the density is a value obtained by rounding off the second decimal point. The density of the specific polymer can be measured, for example, through the method described in the examples below, or can be calculated from the density of each monomer used for synthesis of the specific polymer.

From the viewpoint of setting the density within the above-described preferred range, it is preferable that the specific polymer used in the present invention has an aromatic ring, and it is more preferable that the structural unit (a) having a siloxane bond and/or the structural unit (b) having a urea bond have an aromatic ring.

As the above-described aromatic ring, an aromatic hydrocarbon ring (which may be a monocyclic ring or a condensed ring as long as it shows aromaticity and in which the number of carbon atoms is preferably 6 to 18, more preferably 6 to 14, and still more preferably 6 to 12) is preferable and a benzene ring, a naphthalene ring, an anthracene ring, and a pyrene ring are more preferable.

The content of the specific polymer in the resin composition for an acoustic wave probe is preferably 50 to 100 mass %, more preferably 80 to 100 mass %, and still more preferably 90 to 100 mass %.

The specific polymer used in the present invention preferably has structural units (hereinafter, referred to as "other structural units") other than the above-described structural unit (a) having a siloxane bond and structural unit (b) having a urea bond.

The other structural units can be introduced without particular limitation as long as the effect of the present invention is exhibited, and examples thereof include structural units having any one selected from an amide bond, an imide bond, a urethane bond, an ester bond, and an ether bond.

The proportion of the other structural units in the specific polymer is preferably 0 to 30 mass % and more preferably 0 to 20 mass % from the viewpoint of reducing the acoustic attenuation.

The specific polymer used in the present invention may be used alone or in a combination of two or more thereof.

(Synthesis of Specific Polymer)

Examples of methods for synthesizing the specific polymer used in the present invention include a reaction between a silicone compound having an amino group and a compound having an isocyanate group, a reaction between a silicone compound having an isocyanate group and a compound having an amino group, and a reaction between a silicone compound having a functional group P and a compound which has a urea structure and a functional group having reactivity with the functional group P. As reaction conditions, purification methods, and the like in the method for synthesizing the above-described specific polymer, it is possible to preferably use reaction conditions, purification methods, and the like which are generally used in a urea bond-forming reaction or the like.

Among the above-described synthesis methods, the reaction between a silicone compound having an amino group and a compound having an isocyanate group is preferable from the viewpoint of the availability of raw materials. The polymer obtained through this reaction has a structure in which terminals of $L^1$ and $L^2$ in the structural unit represented by General Formula (1) and the urea bond in the structural unit represented by General Formula (2) are bonded to each other.

Silicone Compound having Amino Group

A silicone compound containing one or more amino groups may be used as the silicone compound having an amino group. From the viewpoints of synthesis suitability and availability of reagents, a silicone compound containing two or more amino groups is preferable and both-terminal amino-modified silicone is more preferable. The silicone compound having an amino group may be used alone or a plurality of silicone compounds having an amino group may be combined.

Examples of the silicone compound having an amino group include PAM-E, KF-8010, X-22-161A, X-22-161B, KF-8012, X-22-1660B-3, and X-22-9409 manufactured by Shin-Etsu Chemical Co., Ltd., DMS-A11, DMS-A12, DMS-A15, DMS-A21, DMS-A31, DMS-A32, DMS-A35, DMS-A211, DMS-A214, AMS-132, AMS-152, and AMS-162 manufactured by GELEST, INC., SF 8417, BY 16-849, BY 16-205, FZ-3760, BY 16-892, FZ-3785, BY 16-872, BY 16-213, BY 16-871, BY 16-853 U, BY 16-891, FZ-3789, KF-868, KF-865, KF-864, KF-859, KF-393, KF-860, KF-880, KF-8004, KF-8002, KF-8005, KF-867, KF-8021, KF-869, KF-861, X-22-3939A, KF-877, KF-889, KF-857, KF-8001, KF-862, KF-858, and X-22-9002 manufactured by Dow Corning Toray Co., Ltd., TSF4700, TSF4701, TSF4702, TSF4703, TSF4704, TSF4705, TSF4706, TSF4707, TSF4708, and TSF4709 manufactured by Momentive, and Silmer NH C-50, Silmer NH Di-8, and Silmer NH Di-50 manufactured by Siltech, all of which are trade names.

Compound having Isocyanate Group

The compound having an isocyanate group may have one or more isocyanate groups. The number of isocyanate groups in the compound is preferably 2 or 3 and more preferably 2. The compound having an isocyanate group may be used alone or a plurality of compounds having an isocyanate group may be combined.

Examples of the compound having two isocyanate groups include (o-, p-, or m-)xylene diisocyanate, tolylene diisocyanate, 4,4'-diphenylmethane diisocyanate, (1,5- or 2,6-) naphthalene diisocyanate, biphenylene diisocyanate, 1,3-bis (2-isocyanato-2-propyl) benzene, 2,2-bis(4-isocyanato phenyl) hexafluoropropane, 3,3'-dichloro-4,4'-diisocyanato biphenyl, 4,4'-diisocyanato-3,3'-dimethyl biphenyl, 1,4-phenylene diisocyanate, 1,3-phenylene diisocyanate, isophorone diisocyanate, trimethylene diisocyanate, hexamethylene diisocyanate, dicyclohexylmethane-4,4'-diisocyanate, and 1,3-bis(isocyanatomethyl) cyclohexane.

Other Copolymerization Components

The specific polymer used in the present invention can be copolymerized by reacting another compound having an amino group different from the above-described silicone compound having an amino group, a compound having a hydroxy group, and the like with each other in addition to the above-described silicone compound having an amino group and compound having an isocyanate group.

In addition, a plurality of compounds can be combined.

The compound having an amino group is not particularly limited as long as it has an amino group, but examples thereof include alkylamine, arylamine, heteroarylamine, and polyethylene imine. In addition, the number of amino groups in the compound is not limited.

The compound having a hydroxy group is not particularly limited as long as it has a hydroxy group, but examples thereof include alkyl alcohol, aryl alcohol, heteroaryl alcohol, polyethylene glycol, and polypropylene glycol. In addition, the number of hydroxy groups in the compound is not limited.

2) Other Additives

The resin composition for an acoustic wave probe of the present invention can be prepared by appropriately formulating organosiloxane such as vinyl silicone and hydrosilicone, filler, a catalyst, a solvent, a dispersing agent, a pigment, a dye, an antistatic agent, a flame retardant, and a thermal conductivity enhancer.

Vinyl Silicone

Any vinyl silicone can be used without particular limitation as long as the vinyl silicone is polyorganosiloxane having a vinyl group. However, the vinyl silicone preferably has two or more vinyl groups in a molecular chain.

Examples of the vinyl silicone include polyorganosiloxane having vinyl groups at least at both terminals of a molecular chain (hereinafter, also simply referred to as vinyl silicone (a)) or polyorganosiloxane having at least two —O—Si(CH$_3$)$_2$(CH=CH$_2$) in a molecular chain (hereinafter, also simply referred to as a vinyl silicone (b)). Among them, the vinyl silicone (a) having vinyl groups at least at both terminals of a molecular chain is preferable.

The vinyl silicone (a) is preferably linear and the vinyl silicone (b) is preferably vinyl silicone (b) in which —O—Si (CH$_3$)$_2$(CH=CH$_2$) is bonded to a Si atom constituting a main chain.

The vinyl silicone is hydrosilylated through a reaction with hydrosilicone having two or more Si—H groups, for example, in the presence of a platinum catalyst. A cross-linked (vulcanized) structure is formed through this hydrosilylation reaction (addition reaction).

The content of vinyl group in the vinyl silicone is not particularly limited. The content of the vinyl group is, for example, preferably 0.01 to 5 mol % and more preferably 0.05 to 2 mol % from the viewpoint of forming a sufficient network with hydrosilicone.

Here, the content of the vinyl group is represented by mol % of the vinyl group-containing siloxane unit based on 100 mol % of all the units constituting the vinyl silicone. One vinyl group-containing siloxane unit has 1 to 3 vinyl groups. Among them, one vinyl group is preferable for one vinyl group-containing siloxane unit. For example, in a case where all Si atoms of Si in a Si—O unit and at a terminal which constitute a main chain have at least one vinyl group, the content becomes 100 mol %.

In addition, the vinyl silicone preferably has a phenyl group, and the content of the phenyl group in the vinyl silicone is not particularly limited. The content of the phenyl group is, for example, preferably 1 to 80 mol % and more preferably 2 to 40 mol % from the viewpoint of mechanical strength in a case where resin for an acoustic wave probe is made.

Here, the content of the phenyl group is represented by mol % of the phenyl group-containing siloxane unit based on 100 mol % of all the units constituting the vinyl silicone. One phenyl group-containing siloxane unit has 1 to 3 phenyl groups. Among them, two phenyl groups are preferable for one phenyl group-containing siloxane unit. For example, in a case where all Si atoms of Si in a Si—O unit and at a terminal which constitute a main chain have at least one phenyl group, the content becomes 100 mol %.

The "unit" refers to Si atoms in a Si—O unit and at a terminal which constitute a main chain.

The degree of polymerization and the specific gravity are not particularly limited. The degree of polymerization is preferably 200 to 3,000 and more preferably 400 to 2,000, and the specific gravity is preferably 0.9 to 1.1 from the viewpoint of improving the mechanical strength, the hardness, the chemical stability, and the like of resin for an acoustic wave probe to be obtained.

The mass average molecular weight of the vinyl silicone is preferably 20,000 to 200,000, more preferably 40,000 to 150,000, and still more preferably 45,000 to 120,000 from the viewpoints of the mechanical strength, the hardness, and/or easiness of processing.

The mass average molecular weight can be measured using, for example, TOLUENE (manufactured by Shonan Wako Junyaku K. K.) as an eluent, TSKgel (registered trademark), G3000HXL+TSKgel (registered trademark), and G2000HXL as columns, and a RI detector under the conditions of a temperature of 23° C. and a flow rate of 1 mL/min after preparing a GPC apparatus HLC-8220 (manufactured by TOSOH CORPORATION).

The kinematic viscosity at 25° C. is preferably $1 \times 10^{-5}$ to 10 m$^2$/s, more preferably $1 \times 10^{-4}$ to 1 m$^2$/s, and still more preferably $1 \times 10^{-3}$ to 0.5 m$^2$/s.

The kinematic viscosity can be measured and obtained at a temperature of 25° C. using a Ubbelohde-type viscometer (for example, a trade name of SU manufactured by SIBATA SCIENTIFIC TECHNOLOGY LTD.) in compliance with JIS Z8803.

Vinyl silicone (a) represented by General Formula (A) is preferable as the polyorganosiloxane (a) having vinyl groups at least at both terminals of a molecular chain.

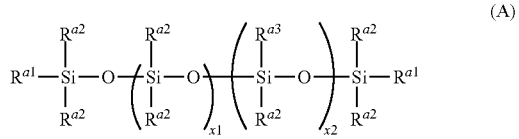

(A)

In General Formula (A), $R^{a1}$ represents a vinyl group and $R^{a2}$ and $R^{a3}$ each independently represent an alkyl group, a cycloalkyl group, an alkenyl group, or an aryl group. x1 and x2 each independently represent an integer of 1 or more. Here, a plurality of $R^{a2}$'s and a plurality of $R^{a3}$'s may be the same as or different from each other. In addition, each of the groups of $R^{a2}$ and $R^{a3}$ may further have a substituent.

The number of carbon atoms in an alkyl group in $R^{a2}$ and $R^{a3}$ is preferably 1 to 10, more preferably 1 to 4, still more preferably 1 or 2, and particularly preferably 1. Examples of the alkyl group include a methyl group, an ethyl group, an n-propyl group, an isopropyl group, an n-butyl group, an isobutyl group, an n-hexyl group, an n-octyl group, a 2-ethylhexyl group, and an n-decyl group.

The number of carbon atoms in a cycloalkyl group in $R^{a2}$ and $R^{a3}$ is preferably 3 to 10, more preferably 5 to 10, and still more preferably 5 or 6. In addition, the cycloalkyl group is preferably a 3-membered ring, a 5-membered ring, or a 6-membered ring, and more preferably a 5-membered ring or a 6-membered ring. Examples of the cycloalkyl group include a cyclopropyl group, a cyclopentyl group, and a cyclohexyl group.

The number of carbon atoms in an alkenyl group in $R^{a2}$ and $R^{a3}$ is preferably 2 to 10, more preferably 2 to 4, and still more preferably 2. Examples of the alkenyl group include a vinyl group, an allyl group, and a butenyl group.

The number of carbon atoms in an aryl group in $R^{a2}$ and $Ra^{a3}$ is preferably 6 to 12, more preferably 6 to 10, and still more preferably 6 to 8. Examples of the aryl group include a phenyl group, a tolyl group, and a naphthyl group.

The alkyl group, the cycloalkyl group, the alkenyl group, and the aryl group may have a substituent. Examples of such a substituent include a halogen atom, an alkyl group, a cycloalkyl group, an alkenyl group, an aryl group, an alkoxy group, an aryloxy group, an alkylthio group, an arylthio group, a silyl group, and a cyano group.

Examples of the group having a substituent include a halogenated alkyl group.

$R^{a2}$ and $R^{a3}$ are preferably an alkyl group, an alkenyl group, or an aryl group, more preferably an alkyl group having 1 to 4 carbon atoms, a vinyl group, or a phenyl group, and still more preferably a methyl group, a vinyl group, or a phenyl group.

Among them, $R^{a2}$ is preferably a methyl group. $R^{a3}$ is preferably a methyl group, a vinyl group, or a phenyl group, more preferably a methyl group or a phenyl group, and particularly preferably a phenyl group. In addition, it is also preferable that both $R^{a2}$'s in the repetition of x1 are phenyl groups.

x1 is preferably an integer of 200 to 3,000 and more preferably an integer of 400 to 2,000.

x2 is preferably an integer of 1 to 3,000, more preferably an integer of 1 to 1,000, still more preferably an integer of 40 to 1,000, and particularly preferably an integer of 40 to 700.

In addition, as another embodiment, x1 is preferably an integer of 1 to 3,000 and more preferably an integer of 5 to 1,000.

Examples of the vinyl silicone (a) having vinyl groups at least at both terminals of a molecular chain include DMS series (for example, DMS-V31, DMS-V31S15, DMS-V33, DMS-V35, DMS-V35R, DMS-V41, DMS-V42, DMS-V46, DMS-V51, and DMS-V52), and PDV series (for example, PDV-0341, PDV-0346, PDV-0535, PDV-0541, PDV-1631, PDV-1635, PDV-1641, and PDV-2335), PMV-9925, PVV-3522, FMV-4031, and EDV-2022 all of which are trade names manufactured by GELEST, INC.

In the DMS-V31S15, fumed silica is formulated into DMS-V31S15 in advance, and therefore, kneading using a special device is unnecessary.

The vinyl silicone may be used singly or in a combination of two or more thereof.

Hydrosilicone

Any hydrosilicone can be used without particular limitation as long as the hydrosilicone is polyorganosiloxane having two or more Si—H groups in a molecular chain.

In a case where there are two or more Si—H groups in a molecular chain, it is possible to crosslink polyorganosiloxane having at least two polymerizable unsaturated groups.

There is hydrosilicone having a linear structure and hydrosilicone having a branched structure in hydrosilicone, and hydrosilicone having a linear structure is preferable.

The mass average molecular weight of hydrosilicone with a linear structure is preferably 500 to 100,000 and more preferably 1,500 to 50,000 from the viewpoints of the mechanical strength and the hardness.

The hydrosilicone which has a linear structure and two or more Si—H groups in a molecular chain is preferably polyorganosiloxane represented by General Formula (B).

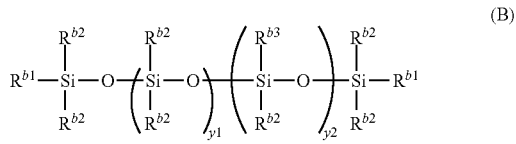

(B)

In General Formula (B), $R^{b1}$ to $R^{b3}$ each independently represent a hydrogen atom, an alkyl group, a cycloalkyl group, an alkenyl group, an aryl group, or —O—Si($R^{b5}$)$_2$ ($R^{b4}$). $R^{b4}$ and $R^{b5}$ each independently represent a hydrogen atom, an alkyl group, a cycloalkyl group, an alkenyl group, or an aryl group. y1 and y2 each independently represent an integer of 1 or more. Here, a plurality of $R^{b1}$'s, a plurality of $R^{b2}$'s a plurality of $R^{b3}$'s, a plurality of $R^{b4}$'s, and a plurality of $R^{b5}$'s each may be the same as or different from each other. In addition, each of the groups of $R^{b1}$ to $R^{b5}$ may further be substituted with a substituent. However, there are two or more Si—H groups in a molecular chain.

An alkyl group, a cycloalkyl group, an alkenyl group, and an aryl group in $R^{b1}$ to $R^{b3}$ are synonymous with an alkyl group, a cycloalkyl group, an alkenyl group, and an aryl group in $R^{a2}$ and $R^{a3}$, and preferred ranges thereof are also the same as each other.

An alkyl group, a cycloalkyl group, an alkenyl group, and an aryl group in $R^{b4}$ and $R^{b5}$ of —O—Si($R^{b5}$)$_2$($R^{b4}$) are synonymous with an alkyl group, a cycloalkyl group, an alkenyl group, and an aryl group in $R^{b1}$ to $R^{b3}$, and preferred ranges thereof are also the same as each other.

$R^{b1}$ to $R^{b3}$ are preferably a hydrogen atom, an alkyl group, an alkenyl group, an aryl group, or —O—Si($R^{b5}$)$_2$($R^{b4}$), and more preferably a hydrogen atom, an alkyl group having 1 to 4 carbon atoms, a vinyl group, a phenyl group, or —O—Si(CH$_3$)$_2$H.

Among them, $R^{b1}$ and $R^{b2}$ are preferably a hydrogen atom, an alkyl group, an alkenyl group, or an aryl group, more preferably a hydrogen atom or an alkyl group, and still more preferably a hydrogen atom or a methyl group.

$R^{b3}$ is preferably a hydrogen atom, an alkyl group, an alkenyl group, an aryl group, or —O—Si($R^{b5}$)$_2$($R^{b4}$), more preferably a hydrogen atom or an aryl group, and still more preferably a hydrogen atom or a phenyl group.

In the present invention, in a case where $R^{b3}$ is a phenyl group, it is preferable that $R^{b1}$ is a hydrogen atom. It is more preferable that $R^{b1}$ is a hydrogen atom and the following conditions are satisfied.

1) One $R^{b2}$ in the repetition of y1 is a hydrogen atom and the remaining $R^{b2}$ is an alkyl group, $R^{b2}$ in the repetition of y2 is an alkyl group, and $R^{b3}$ is a phenyl group.

2) y1 is 0, $R^{2b}$ in the repetition of y2 is an alkyl group, and $R^{b3}$ is a phenyl group.

3) y1 is 0, $R^{b2}$ in the repetition of y2 is —O—Si($R^{b5}$)$_2$($R^{b4}$), and $R^{b3}$ is a phenyl group.

In the above-described 3), a case where $R^{b4}$ is a hydrogen atom and $R^{b5}$ is an alkyl group is particularly preferable.

y1 is preferably an integer of 0 to 2,000, more preferably an integer of 0 to 1,000, and still more preferably an integer of 0 to 30.

y2 is preferably an integer of 1 to 2,000, more preferably an integer of 1 to 1,000, and still more preferably an integer of 1 to 30.

y1+y2 is preferably an integer of 5 to 2,000, more preferably an integer of 7 to 1,000, still more preferably an integer of 10 to 50, and particularly preferably an integer of 15 to 30.

As a combination of $R^{b1}$ to $R^{b3}$, a combination of a hydrogen atom or an alkyl group having 1 to 4 carbon atoms as $R^{b1}$, an alkyl group having 1 to 4 carbon atoms as $R^{b2}$, and a hydrogen atom as $R^{b3}$ is preferable and a combination of an alkyl group having 1 to 4 carbon atoms as $R^{b1}$, an alkyl group having 1 to 4 carbon atoms as $R^{b2}$, and a hydrogen atom as $R^{b3}$ is more preferable.

In the more preferred combinations, the content of a hydrosilyl group represented by y2/(y1+y2) is preferably greater than 0.1 and less than or equal to 1.0 and more preferably greater than 0.2 and less than or equal to 1.0.

Examples of the hydrosilicone with a linear structure include HMS-064 (MeHSiO: 5 to 7 mol %), HMS-082 (MeHSiO: 7 to 8 mol %), HMS-301 (MeHSiO: 25 to 30 mol %), and HMS-501 (MeHSiO: 50 to 55 mol %) as methylhydrosiloxane-dimethylsiloxane copolymers (trimethylsiloxane terminated), HPM-502 (MeHSiO: 45 to 50 mol %) as a methylhydrosiloxane-phenylmethylsiloxane copolymer, and HMS-991 (MeHSiO: 100 mol %) as a methylhydrosiloxane polymer, all of which are trade names of GELEST, INC.

Here, the mol % of MeHSiO has the same meaning as that y2/(y1+y2) in the above-described more preferred combination of $R^{b1}$ to $R^{b3}$ is multiplied by 100.

It is preferable that both the silicone with a linear structure and the silicone with a branched structure have no vinyl group from the viewpoint of preventing the progress of a cross-linking reaction within a molecule. Among these, it is preferable that the silicone with a branched structure has no vinyl group.

The hydrosilicone which has a branched structure and two or more Si—H groups in a molecular chain has a branched structure and two or more hydrosilyl groups (Si—H groups).

The specific gravity is preferably 0.9 to 0.95.

The hydrosilicone with a branched structure is preferably represented by Average Composition Formula (b).

Average Composition Formula (b): [H$_a$(R$^{b6}$)$_{3-a}$SiO$_{1/2}$]$_{y3}$ [SiO$_{4/2}$]$_{y4}$ Here, $R^{b6}$ represents an alkyl group, a cycloalkyl group, an alkenyl group, or an aryl group, a represents 0.1 to 3, and y3 and y4 each independently represent an integer of 1 or more.

An alkyl group, a cycloalkyl group, an alkenyl group, and an aryl group in $R^{b6}$ are synonymous with an alkyl group, a cycloalkyl group, an alkenyl group, and an aryl group in $R^{a2}$ and $R^{a3}$, and preferred ranges thereof are also the same as each other.

a is preferably 1.

The content of a hydrosilyl group represented by a/3 is preferably greater than 0.1 and less than 0.6 and more preferably greater than 0.1 and less than 0.4.

In contrast, in a case of representing the hydrosilicone with a branched structure using a chemical structural formula, polyorganosiloxane in which —O—Si(CH$_3$)$_2$(H) is bonded to a Si atom constituting a main chain is preferable and polyorganosiloxane having a structure represented by General Formula (Bb) is more preferable.

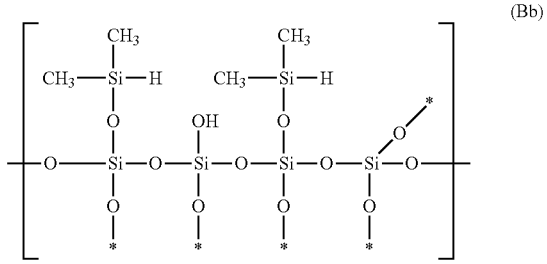

(Bb)

In General Formula (Bb), * means a bond with at least a Si atom of siloxane.

Examples of the hydrosilicone with a branched structure include HQM-107 (trade name of Hydride Q Resin manufactured by GELEST, INC.) and HDP-111 (trade name of polyphenyl-(dimethylhydroxy)siloxane (hydride terminated), [(HM$_{e2}$SiO)(C$_6$H$_5$Si)O]: 99 to 100 mol % manufactured by GELEST, INC.).

The hydrosilicone may be used singly or in a combination of two or more thereof. In addition, a combination of hydrosilicone having a linear structure and hydrosilicone having a branched structure may be used.

The vinyl group possessed by the vinyl silicone and the Si—H group possessed by the hydrosilicone stoichiometrically react with each other in a ratio of 1:1.

However, the equivalent of the Si—H group possessed by the hydrosilicone to the vinyl group possessed by the vinyl silicone from the viewpoint of a reaction between all the vinyl groups with the Si—H groups is preferably vinyl group: Si—H group=1:1.1 to 1:8 and more preferably 1:1.2 to 1:5.

Filler

Since the resin composition for an acoustic wave probe of the present invention does not contain inorganic filler, it is possible to produce a resin sheet having excellent characteristics. However, the resin composition for an acoustic wave probe of the present invention may contain filler.

Any filler that is used in the resin composition for an acoustic wave probe can be used as the filler without particular limitation, and specific examples thereof include inorganic compound particles.

Examples of an inorganic compound in the inorganic compound particles include silicon oxide (silica), silicon carbide, boron nitride, alumina, barium sulfate, cerium oxide, calcium carbonate, aluminum nitride, calcium oxide, vanadium oxide, silicon nitride, barium carbonate, titanium carbide, titanium nitride, copper oxide, zirconium carbide, tungsten carbide, magnesium oxide, titanium oxide, iron oxide, zinc oxide, zirconium oxide, barium oxide, tin oxide, and ytterbium oxide. Any one selected from the group consisting of silica, silicon carbide, boron nitride, alumina, barium sulfate, and cerium oxide is preferable, any one selected from the group consisting of silica, alumina, barium sulfate, and cerium oxide is more preferable, and silica is still more preferable.

In a case where the resin composition for an acoustic wave probe contains the inorganic compound particles, it is possible to obtain an effect of improving the acoustic impedance, the hardness and the mechanical strength of the resin for an acoustic wave probe.

The average primary particle diameter of the inorganic compound particles is preferably greater than 16 nm and less than 100 nm, more preferably 5 nm to 90 nm, still more preferably 10 nm to 80 nm, and particularly preferably 15 nm to 70 nm from the viewpoints of suppressing increase in the acoustic attenuation of the resin for an acoustic wave probe and improving the tear strength.

Here, the average primary particle diameter means a volume average particle diameter. The volume average particle diameter can be obtained by, for example, measuring the particle diameter distribution using a laser diffraction scattering type particle diameter distribution measurement apparatus (for example, trade name "LA910" manufactured by HORIBA, Ltd.). In the present specification, for inorganic compound particles of which the average primary particle diameter has not been disclosed in the catalog or for inorganic compound particles newly manufactured, the average primary particle diameter is obtained through the above-described measurement method.

Here, in a case where surface treatment to be described below is performed, the average primary particle diameter of inorganic compound particles means an average primary particle diameter in a state in which the surface treatment has been performed.

The inorganic compound particles may be used singly or in a combination of two or more thereof.

The specific surface area of the inorganic compound particles is preferably 1 to 400 m$^2$/g, more preferably 5 to 200 m$^2$/g, and particularly preferably 10 to 100 m$^2$/g from the viewpoint of improving the hardness and/or the mechanical strength of resin for an acoustic wave probe to be obtained.

The surfaces of the inorganic compound particles are preferably subjected to surface treatment and more preferably subjected to surface treatment with a silane compound.

By subjecting the inorganic compound particles to surface treatment with a silane compound, an interaction with the polymer used in the present invention which has a siloxane bond becomes stronger and affinity becomes higher. Therefore, it is considered that it is possible to finely disperse inorganic compound particles with a small average primary particle diameter. For this reason, the inorganic compound fine particles more favorably exhibit functions as stoppers in a case where mechanical stress is applied, and therefore, it is considered that the hardness and the mechanical strength of the resin for an acoustic wave probe are improved.

A usual technique may be used as a technique of the surface treatment. Examples of the technique of the surface treatment using a silane compound include a technique of performing surface treatment using a silane coupling agent and a technique of performing coating using a silicone compound.

(i) Silane Coupling Agent

A silane coupling agent having a hydrolyzable group is preferable as a silane coupling agent from the viewpoint of improving the hardness and/or the mechanical strength of resin for an acoustic wave probe. Surface modification of inorganic compound particles is performed such that a hydrolyzable group in a silane coupling agent becomes a hydroxyl group after being hydrolyzed using water and this hydroxyl group is subjected to a dehydration and condensation reaction with a hydroxyl group on the surfaces of the inorganic compound particles, thereby improving the hardness and/or the mechanical strength of obtained resin for an acoustic wave probe. Examples of the hydrolyzable group include an alkoxy group, an acyloxy group, and a halogen atom.

In a case where the surfaces of inorganic compound particles are hydrophobically modified, affinity between the inorganic compound particles, and the vinyl silicone and the hydrosilicone becomes favorable, and therefore, the hardness and the mechanical strength of obtained resin for an acoustic wave probe are improved, which is preferable.

Examples of a silane coupling agent having a hydrophobic group as a functional group include alkoxysilanes such as methyltrimethoxysilane (MTMS), dimethyldimethoxysilane, phenyltrimethoxysilane, methyltriethoxysilane, dimethyldiethoxysilane, phenyltriethoxysilane, n-propyltrimethoxysilane, n-propyltriethoxysilane, hexyltrimethoxysilane, hexyltriethoxysilane, and decyltrimethoxysilane; chlorosilanes such as methyltrichlorosilane, dimethyldichlorosilane, trimethylchlorosilane, and phenyltrichlorosilane; and hexamethyldisilazane (HMDS).

In addition, examples of a silane coupling agent having a vinyl group as a functional group include alkoxysilanes such as methacryloxypropyltriethoxysilane, methacryloxypropyltrimethoxysilane, methacryloxypropylmethyldiethoxysilane, methacryloxypropylmethyldimethoxysilane, vinyltriethoxysilane, vinyltrimethoxysilane, and vinylmethyldimethoxysilane; chlorosilanes such as vinyltrichlorosilane and vinylmethyldichlorosilane; and divinyltetramethyldisilazane.

As the silane coupling agent, a trialkylsilylating agent is preferable and a trimethylsilylating agent is more preferable.

Examples of the silane compound include the above-described silane coupling agents and a silane coupling agent in which a functional group in a silane coupling agent is substituted with an alkyl group.

In addition, examples of the trimethylsilylating agent include trimethylchlorosilane and hexamethyldisilazane (HMDS) described in the above-described silane coupling agent, and methyltrimethoxysilane (MTMS) and trimethylmethoxysilane which are silane coupling agents in which a functional group is substituted with an alkyl group.

Examples of a commercially available silane coupling agent include hexamethyldisilazane (HMDS) (trade name: HEXAMETHYLDISILAZANE (SIH6110.1), manufactured by GELEST, INC.).

A hydroxyl group existing on the surfaces of inorganic compound particles is covered with a trimethylsilyl group through a reaction with hexamethyldisilazane (HMDS), methyltrimethoxysilane (MTMS), trimethylmethoxysilane, and the like and the surfaces of the inorganic compound particles are hydrophobically modified.

In the present invention, the silane coupling agent may be used alone or in a combination of two or more thereof.

(ii) Silicone Compound

A silicone compound with which the inorganic compound particles are coated may be a polymer formed through siloxane bonding.

Examples of the silicone compound include a silicone compound in which all or a part of side chains and/or terminals of polysiloxane has become a methyl group, a silicone compound in which a part of a side chain is a hydrogen atom, a modified silicone compound in which organic groups such as an amino group and/or an epoxy group is introduced into all or a part of side chains and/or terminals, and a silicone resin having a branched structure. The silicone compound may be either of a linear structure or a cyclic structure.

Examples of the silicone compound in which all or a part of side chains and/or terminals of polysiloxane has become a methyl group include monomethylpolysiloxane such as polymethylhydrosiloxane (hydride terminated), polymethylhydrosiloxane (trimethylsiloxy terminated), polymethylphenylsiloxane (hydride terminated), and polymethylphenylsiloxane (trimethylsiloxy terminated); and dimethylpolysiloxanes such as dimethylpolysiloxane (hydride terminated), dimethylpolysiloxane (trimethylsiloxy terminated), and cyclic dimethylpolysiloxane.

Examples of the silicone compound in which a part of side chains is a hydrogen atom include methylhydrosiloxane-dimethylsiloxane copolymer (trimethylsiloxy terminated), methylhydrosiloxane-dimethylsiloxane copolymer (hydride terminated), polymethylhydrosiloxane (hydride terminated), polymethylhydrosiloxane (trimethylsiloxy terminated), polyethylhydrosiloxane (triethylsiloxy terminated), polyphenyl-(dimethylhydrosiloxy) siloxane (hydride terminated), methylhydrosiloxane-phenylmethylsiloxane copolymer (hydride terminated), methylhydrosiloxane-octylmethylsiloxane copolymer, and methylhydrosiloxane-octylmethylsiloxane-dimethylsiloxane terpolymer.

In addition, examples of modified silicone into which an organic group is introduced include reactive silicone into which an amino group, an epoxy group, a methoxy group, a (meth)acryloyl group, a phenol group, a carboxylic anhydride group, a hydroxy group, a mercapto group, a carboxyl group, and/or an organic group of a hydrogen atom are introduced; and non-reactive silicone modified with polyether, aralkyl, fluoroalkyl, long chain alkyl, long chain aralkyl, higher fatty acid ester, higher fatty acid amide, and/or polyether methoxy.

Inorganic compound particles coated with a silicone compound can be obtained through a usual method. For example, the inorganic compound particles can be obtained by being mixed and stirred in dimethylpolysiloxane for a certain period of time and being filtered.

In addition, in a case of using reactive modified silicone as a silicone compound, surface modification of inorganic compound particles is performed through a reaction of an organic group with a hydroxyl group on the surfaces of the inorganic compound particles, and therefore, the hardness and/or the mechanical strength of an obtained resin for an acoustic wave probe is improved.

An Example of the commercially available silicone compound includes methyl hydrogen silicone oil (MHS) (trade name: KF-99, manufactured by Shin-Etsu Chemical Co., Ltd.) which is polymethylhydrosiloxane (trimethylsiloxy terminated).

The degree of surface modification of the inorganic compound particles, that is, the hydrophobicity of the inorganic compound particles can be examined by the following methanol hydrophobicity.

The methanol hydrophobicity of the inorganic compound particles which is calculated through the following methanol titration test is preferably 40 to 80 mass %, more preferably 50 to 80 mass %, and still more preferably 60 to 80 mass %. Here, the larger the methanol hydrophobicity, the higher the hydrophobicity, and the smaller the methanol hydrophobicity, the higher the hydrophilicity.

[Methanol Titration Test]

50 ml of ion exchange water and 0.2 g of inorganic compound particles as samples are placed in a beaker at 25° C. and stirred with a magnetic stirrer, methanol is added dropwise thereto from a burette, and the amount (Xg) of methanol added dropwise until the whole sample settles is measured. The methanol hydrophobicity is calculated using the following equation.

$$\text{Methanol hydrophobicity (mass \%)} = \{X/(50+X)\} \times 100$$

In a case where the methanol hydrophobicity is within the above-described preferred ranges, it is possible to suppress decrease in acoustic sensitivity in a case where a resin sheet for an acoustic wave probe is obtained without increase in the viscosity of the resin composition for an acoustic wave probe before vulcanizing.

The Wardell's sphericity of a primary particle of the inorganic compound particles is preferably 0.7 to 1, more preferably 0.8 to 1, and still more preferably 0.9 to 1.

Here, the "Wardell's sphericity" (refer to Chemical Engineering Handbook published by Maruzen Inc.) is an index obtained by measuring the sphericity of a particle as (diameter of circle equal to projection area of particle)/(diameter of minimum circle circumscribing projection image of particle). A particle having the index closer to 1.0 means a particle closer to a true sphere.

It is possible to use, for example, a scanning electron microscope (SEM) photograph can be used to measure the Wardell's sphericity (hereinafter, also simply referred to as sphericity). Specifically, for example, about 100 primary particles are observed using the SEM photograph, and each sphericity thereof is calculated. An average value obtained by dividing the total of the calculated sphericities by the number of observed primary particles is regarded as the sphericity.

In a case where the Wardell's sphericity is within the above-described preferred ranges, it is considered that the acoustic sensitivity is improved because the area of the acoustic wave hitting the inorganic compound particles becomes smaller in a case where the resin sheet for an acoustic wave probe is irradiated with the acoustic wave. In particular, the shapes of the inorganic compound particles are preferably spherical and more preferably truly spherical in that the acoustic sensitivity is more effectively improved within the ranges of the specific average primary particle diameter of the inorganic compound particles.

In this specification, the "true spherical shape" also includes a slightly distorted sphere of which the Wardell's sphericity is within a range of 0.9 to 1.

Of the inorganic compound particles, the silica particles are roughly classified into combustion method silica (that is, fumed silica) obtained by burning a silane compound, deflagration method silica obtained by explosively burning metallic silicon powder, wet-type silica (among which silica synthesized under alkaline conditions is referred to as precipitation method silica and silica synthesized under acidic conditions is referred to as gel method silica) obtained through a neutralization reaction with sodium silicate and mineral acid, and sol-gel method silica (so-called Stoeber method) obtained through hydrolysis of hydrocarbyloxysilane depending on its production method.

Preferred examples of a method for producing truly spherical silica particles include an explosion method and a sol-gel method.

The sol-gel method is a method of obtaining hydrophilic spherical silica particles essentially consisting of $SiO_2$ units by hydrolyzing and condensing a hydrocarbyloxysilane (preferably tetrahydrocarbyloxysilane) or a partial hydrolytic condensation product thereof or a combination thereof.

In addition, the hydrophobic treatment of the surfaces of the silica particles can also be carried out by introducing $R^3_3SiO_{1/2}$ units ($R^3$'s are the same as or different from each other and are substituted or unsubstituted monovalent hydrocarbon groups having 1 to 20 carbon atoms) onto the surfaces of hydrophilic spherical silica particles.

Specifically, the hydrophobic treatment thereof can be carried out, for example, through methods disclosed in JP2007-99582A and JP2014-114175A.

—Catalyst—

Examples of the catalyst include platinum or a platinum-containing compound (hereinafter, also simply referred to as a platinum compound). Any platinum or platinum compound can be used.

Specific examples thereof include a catalyst in which platinum black or platinum is carried on an inorganic compound, carbon black, or the like; platinum chloride or an alcohol solution of platinum chloride; a complex salt of platinum chloride and olefin; and a complex salt of platinum chloride and vinyl siloxane. The catalyst may be used singly, or in a combination of two or more thereof.

The catalyst is necessary in the hydrosilylation reaction in which the Si—H group of the hydrosilicone is added to the vinyl group of the vinyl silicone. As the hydrosilylation reaction (addition vulcanization reaction) proceeds, vinyl silicone is cross-linked with hydrosilicone to form silicone resin.

Here, the catalyst may be contained in the resin composition for an acoustic wave probe of the present invention or may be brought into contact with the resin composition for an acoustic wave probe without being contained in the resin composition for an acoustic wave probe. The latter case is preferable.

Examples of commercially available platinum catalyst include platinum compounds (a trade name of PLATINUM CYCLOVINYLMETHYLSILOXANE COMPLEX IN CYCLIC METHYLVINYLSILOXANES (SIP6832.2) with 2 mass % of Pt concentration; and a trade name of PLATINUM DIVINYLTETRAMETHYLDISILOXANE COMPLEX IN VINYL-TERMINATED POLYDIMETHYLSILOXANE (SIP6830.3) with 3 mass % of Pt concentration, all of which are manufactured by GELEST, INC.)

In a case where a catalyst is contained in the resin composition for an acoustic wave probe of the present invention, the content of the catalyst present with respect to 100 parts by mass of a polysiloxane mixture (the above-described organosiloxane mixture of vinyl silicone, hydrosilicone, and the like) is not particularly limited, but is preferably 0.00001 to 0.05 parts by mass, more preferably 0.00001 to 0.01 parts by mass, still more preferably 0.00002 to 0.01 parts by mass, and particularly preferably 0.00005 to 0.005 parts by mass from the viewpoint of reactivity.

In addition, it is possible to control the vulcanization temperature by selecting an appropriate platinum catalyst. For example, platinum-vinyldisiloxane is used for room temperature vulcanization (RTV) at lower than or equal to 50° C. and platinum-cyclic vinylsiloxane is used for high temperature vulcanization (HTV) at higher than or equal to 130° C.

—Vulcanization Retardant—

In the present invention, a vulcanization retardant for vulcanization reaction can be appropriately used. The vulcanization retardant is used for delaying the above-described addition vulcanization reaction (hydrosilylation reaction) and examples thereof include a low molecular weight vinyl-methylsiloxane homopolymer (trade name: VMS-005 manufactured by GELEST, INC.)

The vulcanization rate, that is, the working time can be adjusted depending on the content of the vulcanization retardant.

<Method for Producing Resin Composition for Acoustic Wave Probe and Resin Sheet for Acoustic Wave Probe>

The resin composition for an acoustic wave probe of the present invention can be prepared through usual method.

For example, the resin composition for an acoustic wave probe can be obtained by kneading a specific polymer and the above-described other components, which may be contained, using a kneader, a pressure kneader, a Banbury mixer (continuous kneader), and a kneading device with two rolls. The order of mixing the components is not particularly limited.

It is possible to obtain a resin sheet for an acoustic wave probe, for example, by thermally pressing the resin composition for an acoustic wave probe of the present invention which has been obtained in this manner. The thermal press method is not particularly limited, and can be performed through a usual method. An example thereof includes an embodiment in which thermal pressing is performed at 50° C. to 200° C. for 1 to 10 minutes at a pressure of 5 to 30 MPa using an apparatus such as MINI TEST PRESS-10 (a trade name manufactured by Toyo Seiki Seisaku-sho, Ltd.).

<Mechanical Strength and Acoustic Characteristics of Resin Sheet for Acoustic Wave Probe>

The resin sheet for an acoustic wave probe is obtained by molding the resin composition for an acoustic wave probe of the present invention using thermal press or the like.

Hereinafter, the mechanical strength and the acoustic characteristics of a resin sheet for an acoustic wave probe will be described in detail.

Here, ultrasonic characteristics among the acoustic characteristics will be described. However, the acoustic characteristics are not limited to the ultrasonic characteristics, and relates to acoustic characteristics at an appropriate frequency which is selected in accordance with a test object, measurement conditions, and the like.

[Tear Strength]

The tear strength is preferably greater than or equal to 0.5 N/cm, and more preferably greater than or equal to 10 N/cm. A practical upper limit value is less than or equal to 150 N/cm. The tear strength can be measured through the method described in the section of the examples.

[Acoustic Impedance]

The acoustic impedance is preferably close to that of a living body, more preferably $1.1 \times 10^6$ to $1.7 \times 10^6$ kg/m$^2$/sec, and still more preferably $1.3 \times 10^6$ to $1.7 \times 10^6$ kg/m$^2$/sec.

The acoustic impedance of a silicone resin can be obtained through the measurement method described in the section of examples.

[Acoustic (Ultrasonic) Attenuation and Sensitivity]

The acoustic (ultrasonic) attenuation and sensitivity can be measured through the method described in the section of the examples.

In an evaluation system in the present invention, the acoustic (ultrasonic) sensitivity is preferably greater than or equal to −70 dB.

The resin composition for an acoustic wave probe of the present invention is useful for medical members and can preferably be used, for example, in an acoustic wave probe or an acoustic wave measurement apparatus. The acoustic wave measurement apparatus of the present invention is not limited to an ultrasound diagnostic apparatus or a photoacoustic wave measurement apparatus, and is referred to as an apparatus that receives an acoustic wave which has been reflected or generated from an object and displays the received acoustic wave as an image or a signal strength.

Particularly, the resin composition for an acoustic wave probe of the present invention can suitably be used in: a material of an acoustic matching layer which is provided in an acoustic lens of an ultrasound diagnostic apparatus or between a piezoelectric element and the acoustic lens and plays a role of matching acoustic impedance between the piezoelectric element and the acoustic lens; a material of an acoustic lens in a photoacoustic wave measurement apparatus or an ultrasound endoscope; and a material or the like of an acoustic lens in an ultrasound probe including capacitive micromachined ultrasonic transducers (cMUT) as an ultrasonic transducer array.

Specifically, the resin for an acoustic wave probe obtained from the resin composition for an acoustic wave probe of the present invention is preferably applied to, for example, an ultrasound diagnostic apparatus disclosed in JP2005-253751A and JP2003-169802A or an acoustic wave measurement apparatus such as a photoacoustic wave measurement apparatus disclosed in JP2013-202050A, JP2013-188465A, JP2013-180330A, JP2013-158435A, JP2013-154139A, or the like.

<<Acoustic Wave Probe>>

A configuration of an acoustic wave probe of the present invention will be described below in more detail based on a configuration of an ultrasound probe in an ultrasound diagnostic apparatus which is described in FIG. 1. The ultrasound probe is a probe which particularly uses an ultrasonic wave as an acoustic wave in an acoustic wave probe. For this reason, a basic configuration of the ultrasound probe can be applied to the acoustic wave probe as it is.

—Ultrasound Probe—

An ultrasound probe 10 is a main component of the ultrasound diagnostic apparatus and has a function of generating an ultrasonic wave and transmitting and receiving an ultrasonic beam. The configuration of the ultrasound probe 10 is provided in the order of an acoustic lens 1, an acoustic matching layer 2, a piezoelectric element layer 3, and a backing material 4 from a distal end (the surface coming into contact with a living body which is a test object) as shown in FIG. 1. In recent years, an ultrasound probe having a laminated structure in which an ultrasonic transducer (piezoelectric element) for transmission and an ultrasonic transducer (piezoelectric element) for reception are formed of materials different from each other has been proposed in order to receive high-order harmonics.

<Piezoelectric Element Layer>

The piezoelectric element layer 3 is a portion which generates an ultrasonic wave and in which an electrode is attached to both sides of a piezoelectric element. In a case where voltage is applied to the electrode, the piezoelectric element layer generates an ultrasonic wave through repeated contraction and expansion of the piezoelectric element and through vibration.

Inorganic piezoelectric bodies of so-called ceramics obtained by polarizing crystals, single crystals such as $LiNbO_3$, $LiTaO_3$, and $KNbO_3$, thin films of ZnO and AlN, $Pb(Zr,Ti)O_3$-based sintered body, and the like are widely used as the material constituting a piezoelectric element. In general, piezoelectric ceramics such as lead zirconate titanate (PZT) with good conversion efficiency are used.

In addition, sensitivity having a wider band width is required for a piezoelectric element detecting a reception wave on a high frequency side. For this reason, an organic piezoelectric body has been used in which an organic polymer material such as polyvinylidene fluoride (PVDF) is used as the piezoelectric element being suitable for a high frequency or a wide band.

Furthermore, cMUT using micro electro mechanical systems (MEMS) technology in which an array structure, which shows excellent short pulse characteristics, excellent broadband characteristics, and excellent mass productivity and has less characteristic variations, is obtained is disclosed in JP2011-071842A or the like.

In the present invention, it is possible to preferably use any piezoelectric element material.

<Backing Material>

The backing material 4 is provided on a rear surface of the piezoelectric element layer 3 and contributes to the improvement in distance resolution in an ultrasonic diagnostic image by shortening the pulse width of an ultrasonic wave through the suppression of excess vibration.

<Acoustic Matching Layer>

The acoustic matching layer 2 is provided in order to reduce the difference in acoustic impedance between the piezoelectric element layer 3 and a test object and to efficiently transmit and receive an ultrasonic wave.

A resin composition for an acoustic wave probe of the present invention can preferably be used as a material for the acoustic matching layer since the difference in acoustic impedance ($1.4×10^6$ to $1.7×10^6$ kg/m$^2$/sec) between the piezoelectric element layer and a living body is small. The acoustic matching layer preferably contains 10 mass % or more of a resin for an acoustic wave probe obtained from the resin composition for an acoustic wave probe of the present invention.

<Acoustic Lens>

The acoustic lens 1 is provided in order to improve resolution by making an ultrasonic wave converge in a slice direction using refraction. In addition, it is necessary for the acoustic lens to achieve matching of an ultrasonic wave with acoustic impedance ($1.4×10^6$ to $1.7×10^6$ kg/m$^2$/sec in a case of a human body) of a living body which is a test object after being closely attached to the living body and to reduce ultrasonic attenuation of the acoustic lens 1 itself.

That is, sensitivity of transmission and reception of an ultrasonic wave is improved using a material of which the acoustic velocity is sufficiently lower than that of a human body, the ultrasound attenuation is low, and the acoustic impedance is close to a value of the skin of a human body, as the material of the acoustic lens 1.

The resin composition for an acoustic wave probe of the present invention can also preferably be used as a material of the acoustic lens.

The operation of the ultrasound probe 10 having such a configuration will be described. The piezoelectric element layer 3 is resonated after applying voltage to the electrodes provided on both sides of a piezoelectric element, and an ultrasound signal is transmitted to a test object from the acoustic lens. During reception of the ultrasonic signal, the piezoelectric element layer 3 is vibrated using the signal (echo signal) reflected from the test object and this vibration is electrically converted into a signal to obtain an image.

Particularly, a remarkable effect of improving the sensitivity can be checked from a transmission frequency of an ultrasonic wave of greater than or equal to about 5 MHz using the acoustic lens obtained from the resin composition for an acoustic wave probe of the present invention as a general medical ultrasonic transducer. Particularly, a remarkable effect of improving the sensitivity can particularly be expected from a transmission frequency of an ultrasonic wave of greater than or equal to 10 MHz.

Hereinafter, an apparatus in which the acoustic lens obtained from the resin composition for an acoustic wave probe of the present invention exhibits a function particularly regarding conventional problems will be described in detail.

The resin composition for an acoustic wave probe of the present invention exhibits an excellent effect even with respect to other apparatuses disclosed below.

—Ultrasound Probe including Capacitive Micromachined Ultrasonic Transducer (cMUT)—

In a case where cMUT devices disclosed in JP2006-157320A, JP2011-71842A, and the like are used in an ultrasonic diagnostic transducer array, the sensitivity thereof generally becomes low compared to a transducer in which usual piezoelectric ceramics (PZT) is used.

However, it is possible to make up for deficient sensitivity of cMUT using the acoustic lens obtained from the resin composition for an acoustic wave probe of the present invention. Accordingly, it is possible to approximate the sensitivity of cMUT to performance of a conventional transducer.

The cMUT device is manufactured through MEMS technology. Therefore, it is possible to provide an inexpensive ultrasound probe, of which mass productivity is higher than that of a piezoelectric ceramics probe, to the market.

—Photoacoustic Wave Measurement Apparatus using Photo-Ultrasound Imaging—

Photoacoustic imaging (photo acoustic imaging: PAI) disclosed in JP2013-158435A or the like displays a signal strength of an ultrasonic wave or an image obtained by imaging the ultrasonic wave generated in a case where human tissue is adiabatically expanded using light (magnetic wave) with which the interior of a human body is irradiated.

Here, the amount of an acoustic pressure of an ultrasonic wave generated through light irradiation is minute, and therefore, there is a problem in that it is difficult to observe deeper regions of a human body.

However, it is possible to exhibit an effect effective for the problem using the acoustic lens obtained from the resin composition for an acoustic wave probe of the present invention.

—Ultrasound Endoscope—

In an ultrasonic wave in an ultrasound endoscope disclosed in JP2008-311700A or the like, a signal line cable is structurally long compared to that of a transducer for a body surface, and therefore, there is a problem of improving the sensitivity of the transducer accompanied by loss of the cable. Regarding this problem, it is said that there are no effective means for improving the sensitivity due to the following reasons.

First, in a case of an ultrasound diagnostic apparatus for a body surface, it is possible to install an amplifier circuit, an AD conversion IC, or the like at a distal end of the transducer. In contrast, the ultrasound endoscope is inserted into a body. Therefore, there is a small installation space within the transducer, and thus, it is difficult to install the amplifier circuit, the AD conversion IC, or the like at a distal end of the transducer.

Secondly, it is difficult to apply a piezoelectric single crystal employed in the transducer in the ultrasound diagnostic apparatus for a body surface onto a transducer with an ultrasonic transmission frequency of greater than or equal to 7 to 8 MHz due to physical properties and processing suitability. However, an ultrasonic wave for an endoscope is generally a probe having an ultrasonic transmission frequency of greater than or equal to 7 to 8 MHz, and therefore, it is also difficult to improve the sensitivity using piezoelectric single crystal material.

However, it is possible to improve the sensitivity of the endoscope ultrasonic transducer using the acoustic lens obtained from the resin composition for an acoustic wave probe of the present invention.

In addition, even in a case of using the same ultrasonic transmission frequency (for example, 10 MHz), the efficacy is particularly exhibited in a case of using the acoustic lens obtained from the resin composition for an acoustic wave probe of the present invention in the ultrasonic transducer for an endoscope.

EXAMPLE

The present invention will be described in more detail based on Examples in which an ultrasonic wave is used as an acoustic wave. The present invention is not limited to the ultrasonic wave, and any acoustic wave of an audible frequency may be used as long as an appropriate frequency is selected in accordance with a test object, measurement conditions, and the like. Hereinafter, the room temperature means 25° C.

Example (Synthesis of Polymer 1)

23.8 parts by mass of 4,4'-diphenylmethane diisocyanate was added to 76.2 parts by mass of both-terminal amino-modified silicone X-22-161A (a trade name manufactured by Shin-Etsu Chemical Co., Ltd., a molecular weight of 800), 50 parts by mass of tetrahydrofuran, and 50 parts by mass of N-methylpyrrolidone, and the mixture was reacted at room temperature for 1 hour. Thereafter, a white solid was generated by adding the reaction solution to 500 mL of methanol. The generated white solid was washed with water, washed with methanol, and dried to obtain a polymer 1.

In the following chemical reaction formula, ( ) indicates that the structure enclosed in the parentheses is a repeating structure, and m' indicates a repeating number. On the other hand, [ ] indicates that the structure enclosed in the square brackets is a structural unit.

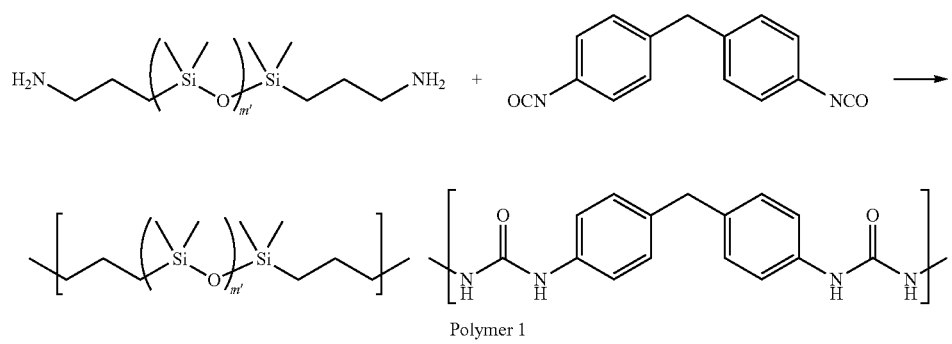

Polymer 1

(Synthesis of Polymers 2 to 12)

Polymers 2 to 12 were obtained in the same manner as in the synthesis of a polymer 1, except that, in the synthesis of Polymer 1, the both-terminal amino-modified silicone, the diphenylmethane diisocyanate, and the reaction time were changed as shown in Table 1.

(Synthesis of Polymer 13)

7.2 parts by mass of 1,5-naphthalene diisocyanate and 22.7 parts by mass of polyethylene glycol (manufactured by Sigma-Aldrich Co. LLC., a molecular weight of 10,000) were added to 70.2 parts by mass of both-terminal amino-modified silicone X-22-1660B-3 (a trade name manufactured by Shin-Etsu Chemical Co., Ltd., a molecular weight of 2,200), 50 parts by mass of tetrahydrofuran, and 50 parts by mass of N-methylpyrrolidone, and the mixture was reacted at room temperature for 24 hours. Thereafter, a white solid was generated by adding the reaction solution to 500 mL of methanol. The generated white solid was washed with water, washed with methanol, and dried to obtain a polymer 13.

TABLE 1

| Polymer No. | Material (1) | | Material (2) | | Material (3) | | Reaction time (hour) |
|---|---|---|---|---|---|---|---|
| | Type | Formulation ratio | Type | Formulation ratio | Type | Formulation ratio | |
| 1 | X-22-161A | 76.2 | MDI | 23.8 | — | — | 1 |
| 2 | DMS-A21 | 95.2 | MDI | 4.8 | — | — | 1 |
| 3 | DMS-A15 | 93.5 | MDI | 6.5 | — | — | 1 |
| 4 | KF-8012 | 89.8 | MDI | 10.2 | — | — | 1 |
| 5 | DMS-A12 | 81.9 | MDI | 18.1 | — | — | 1 |
| 6 | KF-8010 | 63.1 | MDI | 36.8 | — | — | 1 |
| 7 | KF-8012 | 89.8 | MDI | 10.2 | — | — | 6 |
| 8 | KF-8012 | 89.8 | MDI | 10.2 | — | — | 24 |
| 9 | KF-8012 | 92.9 | HDI | 7.1 | — | — | 24 |
| 10 | X-22-1660B-3 | 89.8 | MDI | 10.2 | — | — | 24 |
| 11 | KF-8012 | 91.3 | NDI | 8.7 | — | — | 24 |

TABLE 1-continued

| Polymer No. | Material (1) | | Material (2) | | Material (3) | | Reaction time (hour) |
|---|---|---|---|---|---|---|---|
| | Type | Formulation ratio | Type | Formulation ratio | Type | Formulation ratio | |
| 12 | X-22-1660B-3 | 91.3 | NDI | 8.7 | — | — | 24 |
| 13 | X-22-1660B-3 | 70.2 | NDI | 7.2 | PEO | 22.7 | 24 |

<Notes of Table 1>
Raw materials (1) (all are trade names of both-terminal amino-modified silicone)
X-22-161A: manufactured by Shin-Etsu Chemical Co., Ltd., functional group equivalent of 800 g/mol
KF-8012: manufactured by Shin-Etsu Chemical Co., Ltd., functional group equivalent of 2,200 g/mol
KF-8010: manufactured by Shin-Etsu Chemical Co., Ltd., functional group equivalent of 430 g/mol
X-22-1660B-3: manufactured by Shin-Etsu Chemical Co., Ltd., functional group equivalent of 2,200 g/mol
DMS-A21: manufactured by Gelest, molecular weight of 5,000
DMS-A15: manufactured by Gelest, molecular weight of 3,000
DMS-A12: manufactured by Gelest, molecular weight of 900 to 1,000
Raw materials (2)
MDI: 4,4'-diphenylmethane diisocyanate
HDI: hexylene diisocyanate
NDI: 1,5-naphthalene diisocyanate
Raw materials (3)
PEO: polyethylene oxide (polyethylene glycol) manufactured by Sigma-Aldrich Co. LLC., number average molecular weight of 10,000
The formulation ratio is indicated by a mass ratio.

(Production of Resin Sheets Nos. 101 to 113)

The polymer 1 to 13 obtained above were subjected to thermal press treatment to produce resin sheets Nos. 101 to 113 having a length of 60 mm, a width of 60 mm, and a thickness of 2 mm.

(Production of Resin Sheet No. c11)

96 parts by mass of vinyl terminated polydimethylsiloxane DMS-V41 (a trade name manufactured by Gelest), 4 parts by mass of a methylhydrosiloxane-dimethylsiloxane copolymer HMS-301 (a trade name manufactured by Gelest), and 0.03 parts by mass of a platinum catalyst SIP 6830.3 (a trade name manufactured by Gelest) were mixed with each other and thermally vulcanized at 150° C. for 5 minutes to produce a resin sheet No. c11 which has a length of 60 mm, a width of 60 mm, and a thickness of 2 mm and contains a polymer c1.

(Production of Resin Sheet No. c12)

77 parts by mass of vinyl terminated polydimethylsiloxane DMS-V41 (a trade name manufactured by Gelest), 3 parts by mass of a methylhydrosiloxane-dimethylsiloxane copolymer HMS-301 (a trade name manufactured by Gelest), 20 parts by mass of fumed silica AEROSIL R974 (a trade name manufactured by NIPPON AEROSIL CO., LTD., an average primary particle diameter of 12 nm, dimethyldichlorosilane surface treatment), and 0.05 parts by mass of a platinum catalyst SIP 6830.3 (manufactured by Gelest) were mixed with each other and thermally vulcanized at 150° C. for 5 minutes to produce a resin sheet No. c12 which has a length of 60 mm, a width of 60 mm, and a thickness of 2 mm and contains a polymer c2.

<Physical Properties of Polymer>

[Amount of Urea]

The amount of functional group of urea to be introduced into a polymer was calculated from the amount of monomer charged during synthesis based on the following equation.

Amount of urea (mmol/g)=number of isocyanate groups in one molecule of isocyanate compound×amount of isocyanate monomer (mmol)/total amount of polymer (g)

[Density]

The density of each of the obtained resin sheets with a thickness of 2 mm at 25° C. was measured using an electronic gravimeter (a trade name of "SD-200L" manufactured by ALFA MIRAGE) in accordance with a density measurement method of a method A (underwater substitution method) disclosed in JIS K7112 (1999).

<Evaluation of Mechanical Strength and Ultrasonic Characteristics>

The resin sheets 101 to 113, cll and c12 produced above were evaluated as follows.

[Acoustic (Ultrasonic) Sensitivity]

A sinusoidal signal (a wave) of 10 MHz which had been output from an ultrasound oscillator (a function generator with a trade name of "FG-350" manufactured by IWATSU ELECTRIC CO., LID.) was input into an ultrasound probe (manufactured by JAPAN PROBE), and an ultrasound pulse wave with a center frequency of 10 MHz was generated in water from the ultrasound probe. The magnitude of the amplitude before and after the generated ultrasonic wave passed through each of the obtained resin sheet with a thickness of 2 mm was measured in a water temperature environment of 25° C. using an ultrasound receiver (an oscilloscope with a trade name of "VP-5204A" manufactured by Matsushita Electric Industrial Co., Ltd.). The acoustic (ultrasonic) attenuation of each material was compared with each other by comparing the acoustic (ultrasonic) sensitivities of each material.

The acoustic (ultrasonic) sensitivity is a numerical value given by the following calculation equation.

In the following calculation equation, Vin represents a voltage peak value of an input wave which is generated by the ultrasound oscillator and has a half-width of less than or equal to 50 nsec. Vs represents a voltage value obtained when the ultrasound oscillator receives an acoustic wave (ultrasonic wave) that the acoustic wave (ultrasonic wave) generated passes through a sheet and is reflected from an opposite side of the sheet. The higher the acoustic (ultrasonic) sensitivity is, the smaller the acoustic (ultrasonic) attenuation is.

Acoustic (Ultrasonic) sensitivity=20×Log(Vs/Vin)

The acoustic wave (ultrasonic) sensitivity was evaluated according to the following evaluation criteria. In this test, the evaluation of higher than or equal to "C" is an acceptance level.

<Evaluation Criteria>

AA: Greater than or equal to −64 dB

A: Greater than or equal to −66 dB and less than −64 dB

B: Greater than or equal to −68 dB and less than −66 dB
C: Greater than or equal to −70 dB and less than −68 dB
D: Less than −70 dB

[Acoustic Impedance]

The density of each of the obtained resin sheets with a thickness of 2 mm at 25° C. was measured using an electronic gravimeter (a trade name of "SD-200L" manufactured by ALFA MIRAGE) in accordance with a density measurement method of a method A (underwater substitution method) disclosed in JIS K7112 (1999). In addition, the acoustic velocity of an ultrasonic wave was measured at 25° C. using a sing-around type acoustic velocity measurement apparatus (a trade name of "UVM-2 type" manufactured by Ultrasonic Engineering Co., Ltd.) in compliance with JIS Z2353 (2003). The acoustic impedance was obtained from a sum of the density and the acoustic velocity which had been measured above. The acoustic impedance was evaluated according to the following evaluation criteria. In this test, the evaluation of higher than or equal to "C" is an acceptance level.

<Evaluation Criteria>

A: Greater than or equal to $1.3 \times 10^6$ kg/m$^2$/s
B: Greater than or equal to $1.2 \times 10^6$ kg/m$^2$/s and less than $1.3 \times 10^6$ kg/m$^2$/s
C: Greater than or equal to $1.1 \times 10^6$ kg/m$^2$/s and less than $1.2 \times 10^6$ kg/m$^2$/s
D: Less than or equal to $1.1 \times 10^6$ kg/m$^2$/s

[Tear Strength Test]

A trouser-type test piece of a resin sheet with a thickness of 2 mm was manufactured and the tear strength was measured in compliance with JIS K6252 (2007), and the tear strength was evaluated according to the following evaluation criteria. In this test, the evaluation of higher than or equal to "D" is an acceptance level.

<Evaluation Criteria>

AA: Greater than or equal to 20 N/cm
A: Greater than or equal to 10 N/cm and less than 20 N/cm
B: Greater than or equal to 5 N/cm and less than 10 N/cm
C: Greater than or equal to 1 N/cm and less than 5 N/cm
D: Greater than or equal to 0.5 N/cm and less than 1 N/cm
E: Greater than or equal to 0.1 N/cm and less than 0.5 N/cm
F: Less than 0.1 N/cm The structure and physical properties of polymers are shown in Table 2 and the obtained evaluation results are shown in Table 3.

TABLE 2

| Polymer No. | Structural unit having siloxane bond | | Structural unit having urea bond | | Amount of urea [mmol/g] | Mass average molecular weight [10,000] |
|---|---|---|---|---|---|---|
| | Polysiloxane structure | Proportion [mass %]*1 | Linking group of Urea bond | Proportion [mass %]*1 | | |
| 1 | Dimethylsiloxane | 76 | DPM | 24 | 1.9 | 4.8 |
| 2 | Dimethylsiloxane | 95 | DPM | 5 | 0.4 | 5.0 |
| 3 | Dimethylsiloxane | 93 | DPM | 7 | 0.6 | 5.1 |
| 4 | Dimethylsiloxane | 90 | DPM | 10 | 0.8 | 5.0 |
| 5 | Dimethylsiloxane | 82 | DPM | 18 | 1.7 | 4.9 |
| 6 | Dimethylsiloxane | 63 | DPM | 37 | 2.9 | 5.2 |
| 7 | Dimethylsiloxane | 90 | DPM | 10 | 0.8 | 11.5 |
| 8 | Dimethylsiloxane | 90 | DPM | 10 | 0.8 | 31.0 |
| 9 | Dimethylsiloxane | 93 | 1,6-Hexylene | 7 | 0.8 | 32.0 |
| 10 | Diphenylsiloxane | 90 | DPM | 10 | 0.8 | 35.0 |
| 11 | Dimethylsiloxane | 91 | 1,5-Naphthalenediyl | 9 | 0.8 | 29.5 |
| 12 | Diphenylsiloxane | 91 | 1,5-Naphthalenediyl | 9 | 0.8 | 30.5 |
| 13 | Diphenylsiloxane | 70 | 1,5-Naphthalenediyl | 7 | 0.7 | 31.5 |
| c1 | Dimethylsiloxane | 100*2 | — | — | — | —*3 |
| c2 | Dimethylsiloxane | 80*2 | — | — | — | —*3 |

<Notes of Table>
DPM: diphenylmethane-4,4′-diyl
*1 indicates the proportion of each structural unit in the polymer.
*2 indicates the content ratio in the composition.
*3 Since the polymer has a cross-linked structure, it is impossible to perform measurement.
"—" indicates that the polymer does not contain the corresponding component.

TABLE 3

| Resin sheet No. | Polymer No. | Evaluation | | | | Remarks |
|---|---|---|---|---|---|---|
| | | Density [g/cm$^3$] | Acoustic (ultrasonic) sensitivity | Acoustic impedance | Tear strength | |
| 101 | 1 | 1.03 | B | C | C | Present invention |
| 102 | 2 | 0.98 | AA | C | D | Present invention |
| 103 | 3 | 0.99 | A | C | B | Present invention |
| 104 | 4 | 0.99 | A | C | B | Present invention |
| 105 | 5 | 1.02 | B | C | C | Present invention |

TABLE 3-continued

| Resin sheet No. | Polymer No. | Density [g/cm³] | Acoustic (ultrasonic) sensitivity | Acoustic impedance | Tear strength | Remarks |
|---|---|---|---|---|---|---|
| 106 | 6 | 1.06 | C | B | A | Present invention |
| 107 | 7 | 0.99 | A | C | A | Present invention |
| 108 | 8 | 0.99 | A | C | AA | Present invention |
| 109 | 9 | 0.97 | A | C | A | Present invention |
| 110 | 10 | 1.08 | A | B | AA | Present invention |
| 111 | 11 | 1.01 | A | B | AA | Present invention |
| 112 | 12 | 1.10 | A | A | AA | Present invention |
| 113 | 13 | 1.08 | A | A | AA | Present invention |
| c11 | c1 | 0.98 | A | D | F | Comparative example |
| c12 | c2 | 1.08 | D | B | E | Comparative example |

From Table 3, resin sheets using the resin composition for an acoustic wave probe of the present invention had various excellent performances.

Specifically, a resin sheet No. c11 produced using a comparative composition for an acoustic wave probe which contains polysiloxane having no urea bond had insufficient acoustic impedance and tear strength. In addition, a resin sheet No. c12 produced using a comparative composition for an acoustic wave probe which contains polysiloxane and filler having no urea bond had insufficient acoustic sensitivity and tear strength.

On the other hand, resin sheets Nos. 101 to 113 produced using the resin composition for an acoustic wave probe of the present invention, which contains a polymer having a structural unit having a siloxane bond and a structural unit having a urea bond had both excellent acoustic sensitivity, acoustic impedance, and tear strength.

From the results, it can be seen that the resin composition for an acoustic wave probe of the present invention is useful for a medical member. In addition, it can be seen that the resin for an acoustic wave probe of the present invention can also be suitably used in the acoustic lens of the acoustic wave probe, the acoustic wave measurement apparatus, and the ultrasound diagnostic apparatus. Particularly, the resin composition for an acoustic wave probe of the present invention and the obtained resin for an acoustic wave probe can be suitably used for the purpose of improving the sensitivity in the acoustic wave probe in which cMUT is used as an ultrasonic diagnostic transducer array, the photoacoustic wave measurement apparatus, and the ultrasound endoscope.

The present invention has been described using an embodiment thereof. However, it is considered that, unless otherwise specified, even the detailed description of the invention is not limited and is necessarily widely interpreted without departing from the gist and the range of the invention shown in the attached Claims.

Priority is claimed on JP2016-066427, filed Mar. 29, 2016, and the entire content of which is incorporated herein by reference as a part of the description of the present specification.

EXPLANATION OF REFERENCES

1: acoustic lens
2: acoustic matching layer
3: piezoelectric element layer
4: backing material
7: housing
9: cord
10: ultrasound probe

What is claimed is:

1. An acoustic wave probe comprising:
an acoustic lens comprising a resin composition, the resin composition comprising a polymer which has a structural unit having a siloxane bond and a structural unit having a urea bond.

2. An acoustic wave measurement apparatus comprising:
the acoustic wave probe according to claim 1.

3. An ultrasound diagnostic apparatus comprising:
the acoustic wave probe according to claim 1.

4. A photoacoustic wave measurement apparatus comprising:
an acoustic lens comprising a resin composition, the resin composition comprising a polymer which has a structural unit having a siloxane bond and a structural unit having a urea bond.

5. An ultrasound endoscope comprising:
an acoustic lens comprising a resin composition, the resin composition comprising a polymer which has a structural unit having a siloxane bond and a structural unit having a urea bond.

6. The acoustic wave probe according to claim 1, wherein the structural unit having a siloxane bond is represented by General Formula (1) and the structural unit having a urea bond is represented by General Formula (2)

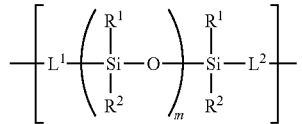

General Formula (1)

-continued

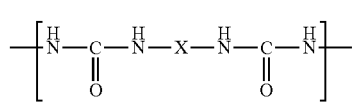

General Formula (2)

in the formulae, $R^1$ and $R^2$ each independently represent a monovalent organic group, $L^1$ and $L^2$ each independently represent a single bond or a divalent linking group, X represents a divalent linking group, and m represents an integer of 1 to 10,000.

7. The acoustic wave probe according to claim 1, wherein an amount of urea in the polymer is 0.2 to 3.0 mmol/g.

8. The acoustic wave probe according to claim 1, wherein a mass average molecular weight of the polymer is greater than or equal to 100,000.

9. The acoustic wave probe according to claim 1, wherein a proportion of the structural unit having a siloxane bond in the polymer is greater than or equal to 70 mass %.

10. The acoustic wave probe according to claim 1, wherein a density of the polymer is greater than or equal to 1.1 g/cm$^3$.

11. The acoustic wave probe according to claim 1, wherein the structural unit having a urea bond has an aromatic ring.

12. The acoustic wave probe according to claim 1, wherein the structural unit having a siloxane bond has an aromatic ring.

\* \* \* \* \*